(12) United States Patent
Szarvas et al.

(10) Patent No.: US 7,547,807 B2
(45) Date of Patent: Jun. 16, 2009

(54) METHOD FOR PRODUCING PHOSPHONIUM SALTS

(75) Inventors: Laszlo Szarvas, Ludwigshafen (DE); Klemens Massonne, Bad Dürkheim (DE); Harald Laas, Maxdorf (DE); Kai Michael Exner, Eppelheim (DE); Detlev Glas, Frankenthal (DE)

(73) Assignee: BASF SE, Ludwigshafen (DE)

( * ) Notice: Subject to any disclaimer, the term of this patent is extended or adjusted under 35 U.S.C. 154(b) by 266 days.

(21) Appl. No.: 10/582,912

(22) PCT Filed: Dec. 14, 2004

(86) PCT No.: PCT/EP2004/014207

§ 371 (c)(1),
(2), (4) Date: Jun. 14, 2006

(87) PCT Pub. No.: WO2005/058924

PCT Pub. Date: Jun. 30, 2005

(65) Prior Publication Data

US 2007/0123726 A1    May 31, 2007

(30) Foreign Application Priority Data

Dec. 17, 2003 (DE) .................................. 103 59 434

(51) Int. Cl.
*C07C 315/00*    (2006.01)
(52) U.S. Cl. ........................................................ 568/9
(58) Field of Classification Search ....................... 568/9
See application file for complete search history.

(56) References Cited

U.S. PATENT DOCUMENTS

| | | | |
|---|---|---|---|
| 3,373,207 A | 3/1968 | Nuerrenbach et al. | |
| 4,105,855 A | 8/1978 | Schulz et al. | |
| 4,182,731 A | 1/1980 | Schulz et al. | |
| 5,344,995 A | 9/1994 | Krause et al. | |
| 5,445,724 A | 8/1995 | Burkhart et al. | |
| 5,689,022 A * | 11/1997 | Paust et al. ................. | 585/351 |

FOREIGN PATENT DOCUMENTS

| | | |
|---|---|---|
| DE | 25 05 869 A1 | 8/1976 |
| DE | 27 27 384 A1 | 1/1979 |
| DE | 27 29 974 A1 | 1/1979 |
| DE | 195 17 422 A1 | 11/1996 |
| EP | 0 579 113 A1 | 1/1994 |
| WO | WO-93/20087 | 10/1993 |

OTHER PUBLICATIONS

Taira et al., 2002, CAS: 138:255045.*
Yamano et al., 2001, CAS: 136:6169.*
Didemnum et al., 1994, CAS: 121:175536.*
Ito et al., 1988, CAS: 110:231910.*
Sliwka et al., 1987, CAS: 109:55001.*
Bestmann et al., 1986, CAS: 105:60777.*

* cited by examiner

*Primary Examiner*—Rei-tsang Shiao
(74) *Attorney, Agent, or Firm*—Connolly Bove Lodge & Hutz LLP

(57) ABSTRACT

The present invention relates to a process for preparing quaternary phosphonium salts by reacting a ternary phosphine with an optionally substituted, saturated or monounsaturated or polyunsaturated electrophile having from 3 to 25 carbon atoms in ternary solvent mixtures.

17 Claims, No Drawings

METHOD FOR PRODUCING PHOSPHONIUM SALTS

CROSS REFERENCE TO RELATED APPLICATIONS

This application is a National Phase of PCT/EP2004/014207, filed Dec. 14, 2004, which claims priority to German patent application 10359434.5 filed Dec. 17, 2003.

The present invention relates to a process for preparing quaternary phosphonium salts by reacting a ternary phosphine with an optionally substituted, saturated or monounsaturated or polyunsaturated electrophile having from 3 to 25 carbon atoms in ternary solvent mixtures.

Quaternary phosphonium salts serve as starting materials or intermediates in the synthesis of monounsaturated or polyunsaturated organic materials of value or active ingredients by the Wittig reaction. Examples of such target compounds are, for instance, terpenes, in particular carotenoids, for example β-carotene, or retinoids, for example vitamin A acetate. These continued to be prepared on the industrial scale by total synthesis. using the Wittig reaction.

A difficulty in the case of phosphonium salt syntheses carried out on an industrial scale is the low solubility of the phosphonium salts in a multiplicity of organic solvents. This frequently leads to them precipitating out in an unwanted manner, which can be accompanied by considerable processing complications. Accordingly, there has been no lack of attempts to prepare solutions of phosphonium salts in polar solvents. However, this always required additional process steps and frequently led to considerable losses in yield. In addition, large amounts of solvent were frequently required, which is scarcely desirable, taking into account the economic aspect and also for reasons of environmental acceptability.

DE-A 27 27 384 discloses a process for preparing aqueous polyenyltriarylphosphonium salt solutions which, inter alia, comprises expelling the organic solvent used in the preparation from the crude product solution using steam.

DE-A 27 29 974, furthermore, describes a process for preparing aqueous finely divided dispersions of polyenyltriarylphosphonium salts in a corresponding manner.

EP-A 0 579 113 relates to a process for preparing cyclic acetals of 3-formyl-2-butenyl-triphenylphosphonium chloride. The substep of reacting the chloride with triphenylphosphine is carried out here in an alkanol having from 1 to 3 carbon atoms and/or an aliphatic or cycloaliphatic hydrocarbon having from 6 to 8 carbon atoms, or in a corresponding hydrocarbon mixture.

DE-A 25 05 869 discloses a process for preparing symmetrical carotenoids from the molecule halves by dimerizing their phosphonium salts in two-phase reaction systems.

It is an object of the present invention to find conditions for preparing organic phosphonium salts under which unwanted precipitation of the phosphonium salts and the disadvantages of the processes known hitherto are avoided.

We have found that this object is achieved in a surprising manner according to the invention by providing a process for preparing quaternary phosphonium salts by reacting a trialkyl-, trialkenyl- or triarylphosphine with an optionally substituted monounsaturated or polyunsaturated aliphatic, cycloaliphatic or aromatic-aliphatic alcohol having from 3 to 25 carbon atoms or its carboxylic acid esters or ethers in the presence of an acid or an optionally substituted aliphatic, cycloaliphatic or aromatic-aliphatic halide having from 3 to 25 carbon atoms, which comprises carrying out the reaction in a ternary solvent mixture.

The inventive process is suitable for preparing quaternary phosphonium salts starting from aliphatic, cycloaliphatic or aromatic-aliphatic alcohols having from 3 to 25 carbon atoms, each of which can be olefinically or acetylenically monounsaturated or polyunsaturated and can bear further functional groups or substituents which are stable under the reaction conditions. It is suitable, moreover, for preparing quaternary phosphonium salts starting from the corresponding carboxylic esters of these alcohols, preferably those which are derived from saturated aliphatic carboxylic acids. In addition, the process is also suitable for preparing quaternary phosphonium salts starting from aliphatic, cycloaliphatic or aromatic-aliphatic halides having from 3 to 25 carbon atoms, which can be saturated or else olefinically or acetylenically monounsaturated or polyunsaturated and furthermore likewise can bear further functional groups or substituents stable under the reaction conditions.

Alternatively, or in supplement thereto, suitable starting materials for the inventive process, in addition to said alcohols, are also the. ethers derived therefrom, where the newly added ether group can comprise from 1 to 6 carbon atoms and is customarily an aliphatic, including also cyclic, or aromatic and optionally substituted group.

The starting compounds to be reacted with a tertiary phosphine according to the invention can be branched or unbranched and comprise cyclic structural elements which themselves can be saturated, unsaturated or aromatic, the individual structural elements themselves being able to bear substituents, for example halogen atoms, alkyl groups having from 1 to 7 carbon atoms, such as methyl, ethyl, propyl, isopropyl, n-butyl, t-butyl, pentyl and/or hexyl, or else heteroatoms such as N, O which themselves can bear further substituents. As in the context of the entire present invention halogen here is F, Cl or Br. Further preferred substituents which may be mentioned are, for example, amines such as $NH_2$, dibenzylamine and dimethylamine or else oxygen-bonded substituents, for example methoxy, acetoxy or benzyloxy. In addition, the starting compounds can also comprise functional groups stable under the reaction conditions, for example carbonyl functions, especially keto-carbonyl functions, which if appropriate can also be α,β-unsaturated or can be in the α- or β-position to a hydroxyl or acetoxy group, or else ester or nitrile functions.

The above-described monounsaturated or polyunsaturated alcohols, halides, esters and ethers which are suitable for the inventive reaction to form quaternary phosphonium salts are also called electrophiles in the context of the present invention in accordance with their chemical reaction behavior.

All of the olefinically monounsaturated or polyunsaturated compounds mentioned in the context of the present invention can be present or used or obtained in the form of their respective possible double-bond isomers or in the form of mixtures of same.

The starting compounds are reacted according to the invention with a tertiary phosphine. The structure of the organic groups of the phosphine is not critical here and can be varied over a broad range. For instance, the organic radicals of the phosphine can be selected from the groups of the alkyl, alkenyl or aryl radicals having from 1 to 9 carbon atoms and within these groups can be identical or different, preferably identical. Furthermore, said radicals can themselves be substituted, for example by one or more halogen atoms, or else one or more alkyl radicals having from 1 to 4 carbon atoms, for example methyl, ethyl, isopropyl and/or tert-butyl. Examples of suitable phosphines are, inter alia, trimethyl-, triethyl- and triallylphosphine, and also triphenyl-, tri-paratolyl-, tri-ortho-tolyl- and trimesitylphosphine. A particularly preferred tertiary phosphine is triphenylphosphine.

To carry out the inventive process, the electrophile selected is reacted in a ternary solvent mixture. In the context of the present invention, a ternary solvent mixture is a composition of matter which comprises three different solvent components and. preferably consists of three different solvent components. The individual components are preferably distinguished by a differing polarity or differing solvent properties. They can be completely or partially miscible with one another and form a mixture which can be single-phase or, in the case of partially miscible components, can be two-phase or multiphase. The reaction to be carried out in the context of the inventive process can occur in one or more of the phases present, independently of one another.

Suitable solvent components which may be mentioned by way of example are: water, alcohols having from 1 to 6 carbon atoms and 1, 2 and/or 3 hydroxyl functions, for example methanol, ethanol, propanol, isopropanol, 1-butanol, 2-butanol, glycol, 1,2-propanediol, 1,3-propanediol or mixtures of same and hydrocarbons having from 5 to 12 carbon atoms or mixtures of same. Suitable hydrocarbons can be branched or unbranched aliphatic, cyclic, cycloaliphatic, aromatic and aromatic-aliphatic. Examples of these which may be mentioned are: n-pentane, n-hexane, cyclohexane, methylcyclohexane, 1,2-dimethylcyclohexane, 1,3-dimethylcyclohexane, 1,4-dimethylcyclohexane, ethylcyclohexane, 2-methylhexane, 3-methylhexane, n-heptane, cycloheptane, methylcycloheptane, n-octane, benzene, toluene, ortho-xylene, meta-xylene, para-xylene or mixtures of same.

In the context of the present invention it has also proved to be advantageous when water is used as one of the solvent components. In addition it has proved to be advantageous, in addition to water as first component, to use as second component an alcohol, for example methanol or ethanol, and as third component a hydrocarbon. It is not necessary in this case to use the individual components in pure form. For instance, it can occasionally be advantageous to use, as hydrocarbon component, a mixture of various hydrocarbons, for example a mixture of various isomers of heptane or else hydrocarbon blends consisting of hydrocarbons having from 6 to 8, preferably having 6 or 7, particularly preferably having 7, carbon atoms. Typical constituents of such a $C_7$ blend, also to be termed technical heptane or in the context of the present invention heptane, customarily comprise at least one of the following compounds: hexane, heptane, octane, isooctane, cyclohexane, toluene, cyclopentane, methylcyclopentane, dimethylcyclopentane (1,1-, 1,2-, 1,3-), ethylcyclopentane, 2-methylhexane, 3-methylhexarie, 2-methylheptane, 3-methylheptane, 4-methylheptane, 2-ethylhexane, 3-ethylhexane, methylcyclohexane, dimethylcyclopentanes (1,1-, 1,2-, 1,3-) and more of the like. In addition, the hydrocarbon component selected can also comprise aromatic and/or aliphatic-aromatic minor components, if these have not already been selected as hydrocarbon component.

Comparable considerations can also be applied to the further components of the solvent mixture to be used according to the invention. Thus, as alcohol component, for example, an alcohol can be selected, for example methanol ethanol or n-propanol or isopropanol, which comprises, as minor components or impurities, further of the abovementioned alcohols. The alcohol component selected can also comprise water, which then is to be added in calculation to the water component of the inventive ternary solvent mixture. Here, the customary small water contents of the technical solvents are not to be assessed as an independent third component of the solvent mixture. One example of a water-comprising alcohol is methanol which can comprise up to about 40% by weight of water. Such a methanol is to be considered as a preferred solvent for the alcohol component of the ternary solvent mixtures to be used according to the invention.

If water is selected as a component of the ternary solvent, it has proved to be advantageous if the finished ternary solvent mixture consists, overall, of at least about 5% by weight of water, preferably of at least about 10% by weight.

Good results are generally achieved if, as further components, methanol and heptane are selected as described above. In the context of the present invention, preferred solvent mixtures therefore consist of water, methanol and heptane, in which case methanol can be used in non-predried form, heptane is a mixture of isomers as described above and the finished solvent mixture consists of at least about 5% by weight, preferably of at least about 10% by weight, of water.

The proportions of the alcohol component or hydrocarbon component can be chosen freely in principle within broad limits. It has proved to be expedient to use the alcohol component as main component, considered quantitatively. Advantageously, solvent mixtures are used which comprise at least about 50% by weight of the alcohol component, preferably consist of methanol, and in addition comprise at least about 10% by weight of water. In the context of the inventive process, particularly preferred ternary solvent mixtures consist of approximately 55-85% by weight of methanol 10-25% by weight of heptane and 5-20% by weight of water, in which case the proportions chosen within said ranges must total 100% by weight.

The ternary solvent mixtures which can be used in the context of the inventive process can form, as already mentioned, single-, two- and if appropriate also multiphase mixtures. Preferably, mixtures are used which are present in the form of two-phase mixtures, generally in the form of an aqueous phase and an organic phase.

The inventive process is suitable in particular for preparing quaternary phosphonium salts of the general formula I $$[R^1\text{-}P(R^2)_3]^{3\oplus}X^-\quad\quad\quad(I),$$

where

R$^1$ is an optionally substituted monounsaturated or polyunsaturated aliphatic, cycloaliphatic or aromatic-aliphatic group having from 3 to 25 carbon atoms, R$^2$ is an alkyl, alkenyl or aryl group having from 1 to 9 carbon atoms and X is the anion equivalent of an organic or inorganic acid, by reacting a phosphine of the general formula II $$P(R^2)_3\quad\quad\quad(II),$$

where R$^2$ has the meaning given above, with a monounsaturated or polyunsaturated electrophile of the general formula III or IV,

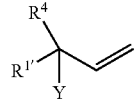

where $R^1$ has the meaning given above and
$R^{1'}$ is an optionally substituted, aliphatic, cycloaliphatic or aromatic-aliphatic hydrocarbon group having from 1 to 21 carbon atoms,
Y is OH, Cl, Br, O(CO)$R^3$ or O$R^3$ and $R^3$ is an aliphatic hydrocarbon group having from 1 to 6 carbon atoms and
$R^4$ is H or CH$_3$
and, when an electrophile of the general formula IV is reacted, $R^1$ in formula I is a structural element of the general formula V

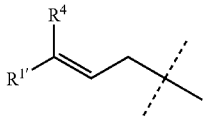

(V)

where $R^{1'}$ and $R^4$ have the meanings given above.

Examples of suitable phosphines which may be mentioned are: trimethyl-, triethyl- and triallylphosphine and also triphenyl-, tri-para-tolyl-, tri-ortho-tolyl- and trimesitylphosphine. Leaving groups Y of the general formulae III and IV which may be mentioned are preferably: OH, Cl, Br, OR$^3$ or O(CO)$R^3$, that is to say an ester derived from an acid $R^3$COOH and an alcohol, where $R^3$ is an aliphatic hydrocarbon radical having from 1 to 6 carbon atoms. Particular preference among these is given to the esters derived from acetic acid.

In a particularly preferred embodiment, the inventive process is suitable for preparing quaternary phosphonium salts of the general formula I'

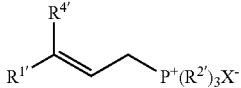

(I')

where
$R^{1'}$ has the meaning given above,
$R^{2'}$ is an aryl group having from 1 to 9 carbon atoms,
$R^{4'}$ is H or CH$_3$ and
X is the anion equivalent of an organic or inorganic acid,
by reacting a phosphine of the general formula II'

P(R$^{2'}$)$_3$ (II'), where $R^{2'}$ has the meaning given above, with an optionally substituted monounsaturated or polyunsaturated electrophile of the general formula IV or VI,

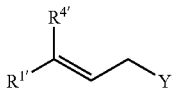

(VI)

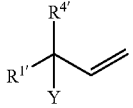

(IV)

where $R^{1'}$ and $R^{4'}$ have the meanings given above and Y has the meaning given for formula III and formula IV.

By way of example, as electrophiles useable according to the invention the compounds hereinafter may be mentioned, where the alcohols mentioned can also be used in the form of their chlorides or bromides and where if appropriate hydroxyl and/or carbonyl functions present can also be in protected form, for example as acetals, ketals and/or ethers: retinol, retinol acetate (vitamin A acetate), βvinylionol, 3,7,11-trimethyidodeca-1,4,6,10-tetraen-3-ol, 1,1-dimethoxy-2-methylbut-3-en-2-ol, 6-hydroxy-3-(7-hydroxy-3,7-dimethyinona-1,3,5,8-tetraenyl)-2,4,4-trimethylcyclohex-2-enone, 4-(7-hydroxy-3,7-dimethylnona-1,3,5,8-tetraenyl)-3,5,5-trimethylcyclohex-3-enol, but-2-ene-1,4-diol, 1,4-dibromobut-2-ene, 1,4-dichlorobut-2-ene, 4-hydroxy-2-methylbut-2-enal, 4-bromo-2-methylbut-2-enal, 4-chloro-2-methylbut-2-enal, 4-acetoxy-2-methyl-but-2-enal, 4-methoxy-2-methylbut-2-en-1-ol, 3,7,11-trimethyidodeca-2,4,6,10-tetraen-1-ol, 4-hydroxy-3-methylbut-2-enoic acid methyl ester, 4-bromo-3-methylbut-2-enoic acid methyl ester, 4-chloro-3-methyl-but-2-enoic acid methyl ester, 2-hydroxy-2-methylbut-3-enoic acid ethyl ester, 2-bromo-2-methylbut-3-enoic acid ethyl ester, 2-chloro-2-methylbut-3-enoic acid ethyl ester, 6-hydroxy-3-(5-hydroxy-3-methylpent-3-en-1-ynyl)-2,4,4-trimethylcyclohex-2-enone, 6-acetoxy-3-(5-hydroxy-3-methylpent-3-en-1-ynyl)-2,4,4-trimethylcyclohex-2-enone, 6-chloro-3-(5-hydroxy-3-methylpent-3-en-1-ynyl)-2,4,4-trimethylcyclohex-2-enone, 4-(5-hydroxy-3-methylpent-3-en-1-ynyl)-3,5,5-trimethylcyclohex-3-enol, 4-(5-chloro-3-methylpent-3-en-1-ynyl) -3,5,5-trimethyl-cyclohex-3-enol, 4-(5-acetoxy-3-methylpent-3-en-1-ynyl)-3,5,5-trimethylcyclohex-3-enol, 6-hydroxy-3-(5-hydroxy-3-methylpenta-1,3-dienyl)-2,4,4-trimethylcyclohex-2-enone, 6-hydroxy-3-(5-chloro-3-methylpenta-1,3-dienyl)-2,4,4-trimethylcyclohex-2-enone, 6-hydroxy-3-(5-bromo-3-methylpenta-1,3-dienyl)-2,4,4-trimethylcyclohex-2-enone, 6-chloro-3-(5-chloro-3-methylpenta-1,3-dienyl)-2,4,4-trimethylcyclohex-2-enone, 6-hydroxy-3-(5-bromo-3-methylpenta-1,3-dienyl)-2,4,4-trimethylcyclohex-2-enone, 6-acetoxy-3-(5-hydroxy-3-methylpenta-1,3-dienyl)-2,4,4-trimethylcyclohex-2-enone, 6-hydroxy-3-(5-aetoxy-3-methylpenta-1,3-dienyl)-2,4,4-trimethylcyclohex-2-enone, 4-(5-hydroxy-3-methylpenta-1,3-dienyl)-3,5,5-trimethylcyclohex-3-enol, 4-(5-chloro-3-methylpenta-1,3-dienyl)-3,5,5-trimethylcyclohex-3-enol, 4-(5-bromo-3-methylpenta-1,3-dienyl)-3,5,5-trimethylcyclohex-3-enol, 4-(5-acetoxy-3-methylpenta-1,3-dienyl)-3,5,5-trimethylcyclohex-3-enol, 6-hydroxy-3-(9-hydroxy-3,7-dimethyinona-1,3,5,7-tetraenyl)-2,4,4-trimethylcyclohex-2-enone, 6-acetoxy-3-(9-hydroxy-3,7-dimethylnona-1,3,5,7-tetraenyl)-2,4,4-trimethylcyclohex-2-enone, 5-hydroxy-3-(9-hydroxy-3,7-dimethylnona-1,3,5,7-tetraenyl)-2,4,4-trimethylcyclohex-2-enone, 5-acetoxy-3-(9-hydroxy-3,7-dimethylnona-1,3,5,7-tetraenyl)-2,4,4-trimethylcyclohex-2-enone, 4-(9-hydroxy-3,7-dimethylnona-1,3,5,7-tetraenyl)-3,5,5-trimethylcyclohex-3-enol, 4-(9-acetoxy-3,7-dimethylnona-1,3,5,7-tetraenyl)-3,5,5-trimethylcyclohex-3-enol, 3-methyl-1-(2,2,6-trimethyl-7-oxabicyclo[2.2.1]hept-1-yl)-penta-1,4-dien-3-ol and 6-hydroxy-3-(3-hydroxy-3-methyl-1,4-pentadienyl)-2,4,4-trimethylcyclohex-2-enone.

Preferred electrophiles are, for example: retinol, retinol acetate (vitamin A acetate), β-vinylionol, 3,7,11-trimethyidodeca-1,4,6,10-tetraen-3-ol, 1,4-dibromobut-2-ene, 1,4-dichlorobut-2-ene, 4-bromo-2-methylbut-2-enal, 4-chloro-2-methylbut-2-enal, 4-acetoxy-2-methylbut-2-enal, 2-bromo-2-methylbut-3-enoic acid ethyl ester, 2-chloro-2-methylbut-3-enoic acid ethyl ester, 6-hydroxy-3-(5-hydroxy-3-methylpent-3-en-1-ynyl)-2,4,4-trimethylcyclohex-2-enone, 6-acetoxy-3-(5-hydroxy-3-methylpent-3-en-1-ynyl)-2,4,4- trimethylcyclohex-2-enone, 4-(5-hydroxy-3-methylpent-3-en-1-ynyl)-3,5,5-trimethylcyclohex-3-enol, 4-(5-chloro-3-methylpent-3-en-1-ynyl)-3,5,5-trimethylcyclohex-3-enol, 6-hydroxy-3-(5-hydroxy-3-methylpenta-1, 3-dienyl)-2,4,4-trimethylcyclohex-2-enone, 6-hydroxy-3-(5-chloro-3-methylpenta-1,3-dienyl )-2,4,4-trimethylcyclohex-2-enone, 6-hydroxy-3-(5-bromo-3-methylpenta-1,3-dienyl )-2,4,4-trimethylcyclohex-2-enone, 4-(5-hydroxy-3-methylpenta-1,3-dienyl)-3,5,5-trimethylcyclohex-3-enol, 4-(5-chloro-3-methylpenta-1,3-dienyl)-3,5,5-trimethylcyclohex-3-enol, 4-(5-bromo-3-methylpenta-1,3-dienyl)-3,5,5-trimethylcyclohex-3-enol, 3-methyl-1-(2,2,6-trimethyl-7-oxabicyclo[2.2. 1]hept-1-yl)penta-1,4-dien-3-ol and 6-hydroxy-3-(3-hyd roxy-3-methyl-1,4-pentadienyl)-2,4,4-trimethylcyclohex-2-enone.

As examples of phosphonium salts of the general formula I which are accessible by the inventive process, those may be mentioned, in particular, which can serve as starting materials or intermediates for synthesis of compounds of the carotenoid or retinoid series by Wittig olefination: examples of these are, inter alia: β-ionylideneethyl-triphenylphosphonium hydrogensulfate or hydrogen chloride, axerphtylphosphonium hydrogensulfate or hydrogen chloride, 3,7,11,15-tetramethylhexadeca-2,4,6,8,10,14-hexaen-yl-1-triphenylphosphonium hydrogensulfate or hydrogen chloride, 5-(2',6',6'-trimethylcyclohexen-1'-yl-1')-3-methylpentadien-2,4-yl-1-triphenylphosphonium hydrogensulfate or hydrogen chloride, 9-[2',6',6'-trimethylcyclohexen-1'-yl-1']-3,7-dimethyl-2,6,8-nonatrien4-yn-1-yl-triphenylphosphonium bromide, 3,7,11,15-tetramethylhexadeca-2,4,6,8,10-pentaen-1-yl-triphenylphosphonium hydrogensulfate and also other phosphonium salts mentioned in DE-A 25 05 869.

The inventive reaction of alcohols, ethers and esters with the selected tertiary phosphine is advantageously carried out in the presence of an organic or inorganic acid. Suitable acids are, in particular, hydrochloric acid, sulfuric acid, hydrobromic acid, formic acid, acetic acid, propionic acid or phosphoric acid, methanesulfonic acid, trifluoromethansulfonic acid, para-toluenesulfonic acid, benzenesulfonic acid or else trifluoroacetic acid, preferably hydrochloric acid and sulfuric acid. These are customarily used in an amount of from about 0.9 to about 1.1 equivalents, based on the amount of phosphine used. The counterions X of the phosphonium salts of the general formula I prepared in the context of the inventive process are customarily formed by the anion equivalents of said acids, in particular of hydrochloric, sulfuric and hydrobromic acid.

In the case of the inventive reaction of organic halides as electrophile, the counterion X of said phosphonium salts of the general formula I is customarily formed by the substituted halide ion, in particular Cl or Br.

A very particularly preferred embodiment of the inventive process is that wherein, to prepare quaternary phosphonium salts of the formula I"

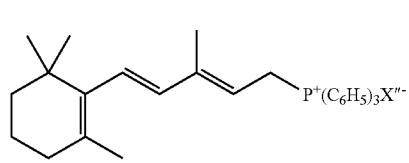

(I")

where

X" is Cl, Br or HSO$_4$, triphenylphosphine is reacted with β-vinylionol in a manner according to the invention.

No particular requirements are to be made of the reaction conditions under which the inventive process is customarily carried out. For instance, reaction temperature, concentrations of the starting materials in the solvent mixture selected, reaction times and also purity of the reagents used, for example, generally vary in ranges which are sufficiently known to those skilled in the art and can be looked up, for example in Houben-Weyl, "Methoden der Organischen Chemie" [Methods of organic chemistry], Volume 12/1, Thieme, Stuttgart, 1963 and Volume E1, Thieme, Stuttgart, 1982 or else in Johnson, Kaska, Starzewski, Pixon "Ylides and Imines of Phosphorus", Wiley, New York, 1993.

Customarily, the electrophile to be reacted is used in a purity of from about 50 to about 99%. The phosphine selected is generally used in a purity of from about 80 to about 99.5% and in about equimolar ratio to the electrophile, that is to say at from about 0.9 to 1.1 equivalents based on the amount of electrophile. If an alcohol or an ester is reacted as electrophile, the reaction is advantageously carried out, as already mentioned, in the presence of an organic or inorganic acid. Preferably, hydrochloric acid is used, customarily in the form of a from about 10 to about 36% strength by weight aqueous solution, or sulfuric acid in the form of a from about 70 to about 98% strength by weight aqueous solution. Preferably, use is made of aqueous sulfuric acid, in particular that having a concentration of from about 70 to about 80% by weight. The acid selected is customarily used in an amount of from about 0.9 to about 1.2 equivalents, based on the amount of electrophile to be reacted.

The reaction procedure does not differ in principle from the procedures in the processes known to those skilled in the art. Customarily, the phosphine is charged in the ternary solvent mixture selected, and then, in the case of the reaction of alcohols or esters as electrophile, the acid is added. Other sequences of addition are also possible, however. The acid is usually added slowly, possibly dropwise, and at temperatures of from about room temperature to about 70° C. The acid addition is then customarily completed after about 1 to about 10 h. The electrophile to be reacted can be added simultaneously or staggered in time, customarily after addition of the acid is completed, and is usually performed within the same temperature range and is usually completed likewise after from 1 to 10 h. To complete the conversion, the reaction mixture is usually further post-stirred at temperatures in the range specified.

No particular requirements are to be made of the reaction vessel or the reactor. The reaction mixture can be worked up, and the reaction product isolated, according to methods known per se to those skilled in the art.

Particularly advantageously, the ternary solvent mixture used according to the invention, after reaction is completed, is separated from the remaining constituents of the reaction mixture and it is recirculated back to the reaction process. It can be necessary here that the original composition of the ternary solvent mixture must be restored. This is expediently performed by adding one or two components of the solvent mixture selected. Obviously, any other composition differing from the composition originally selected can also be set in this manner.

By means of the process described the desired phosphonium salts are obtained customarily in excellent yields and high purity, which, especially for reactions on an industrial scale, is a particular advantage. However, in principle, the process can be carried out with good success on any scale.

A further particular advantage of the inventive process is that, by means of the suitable composition of the ternary solvent mixture, the unwanted precipitation or crystallization of the phosphonium salts to be synthesized can generally be very largely prevented. As a result, the process described is also particularly suitable for industrial scale reactions carried out continuously.

The inventive process is particularly suitable for preparing quaternary phosphonium salts which are valuable starting materials or intermediates for preparing polyisoprenoids, carotenoids and retinoids.

The invention therefore also relates to the use of phosphonium salts prepared according to the inventive process for preparing polyisoprenoids, in particular retinol (vitamin A), vitamin A acetate, vitamin A propionate, vitamin A palmitate, retinal, retinoic acids, β-carotene, α-carotene, δ-carotene, zeaxathin, astaxanthin, canthaxanthin, lycopene, citranaxanthin, β-apo-8'-carotenal, crocetin, α-crypotoxanthin, β-crypotoxahthin, phytoene, lutein, bixin, capsanthin, capsorubin, β-apo-8'-carotenoic acid methyl ester, β-apo-8'-carotenoic acid ethyl ester, β-apo-8'-carotenoic acid propionyl ester, β-apo-8'-carotenoic acid paimityl ester.

The examples hereinafter serve to illustrate the invention, but without restricting it in any manner:

EXAMPLE 1

Preparation of β-ionolidenetriphenylphosphonium hydrogensulfate in a ternary solvent mixture 139.7 g of triphenylphosphine were charged at 40° C. with stirring in a solvent mixture consisting of 206.8 g of methanol, 44.46 g of water and 40.68 g of heptane. In the course of 1 h, 72.7 g of 75% strength sulfuric acid were added dropwise. Then, 130 g of β-vinylionol of a purity of 92.1% were added in the course of 2 h, the temperature was raised to 50° C. and the mixture further stirred for 4 h. After workup by extraction, β-ionolidenetriphenylphosphonium hydrogensulfate was obtained in a yield of 99.9% (based on triphenylphosphine used).

COMPARATIVE EXAMPLE 1

Preparation of β-ionolidenetriphenylphosphonium hydrogensulfate in acetone 90.8 g of triphenylphosphine were charged with stirring in 396 g of acetone, and 36.9 g of 96% strength sulfuric acid and 8.45 g of 92.1% strength β-vinylionol were added dropwise simultaneously at a temperature of 37° C. in the course of 2 h. After 90 min, crystallization began. The mixture was further stirred at 25° C. for 3 h, then cooled to 15° C. and finally filtered with suction. This produced β-ionolidenetriphenylphosphonium hydrogensulfate in an amount of 134.6 g equivalent to 69.2% of theory (based on triphenylphosphine used).

COMPARATIVE EXAMPLE 2

Preparation of β-ionolidenetriphenylphosphonium hydrogensulfate in methanol 181.6 g of triphenylphosphine were charged with stirring in 396 g of methanol at a temperature of 60° C. and 73.75 g of a 96% strength sulfuric acid were added in the course of 1 hour and then 169 g of 92.1% strength β-vinylionol were added in the course of 10 min. The mixture was further stirred at 60° C. for 1 h and then worked up by extraction. This produced 375 g of β-ionolidenetriphenylphosphonium hydrogensulfate equivalent to 96.3% of theory (based on triphenylphosphine used). With a further stirring time of 4 h, the yield of the target compound decreased to 95.5% of theory.

COMPARATIVE EXAMPLE 3

Preparation of β-ionolidenetriphenylphosphonium hydrogensulfate in a methanol/water mixture 585.5 g of triphenylphosphine were charged with stirring in a mixture of 1014.2 g of methanol and 221.4 g of water at a temperature of 40° C. Then, 304.7 g of a 75% strength sulfuric acid were added dropwise in the course of 1 h and, subsequently thereto, 544.8 g of 92.1% strength β-vinylionol were added in the course of 4 h at a temperature of 50° C. The batch was further stirred for 4 h at 50° C. and worked up by extraction. This produced the target compound in a yield of 97.9% of theory (based on triphenylphosphine used).

We claim:

1. A process for preparing a quaternary phosphonium salt comprising reacting a trialkyl-, trialkenyl- or triarylphosphine with an optionally substituted monounsaturated or polyunsaturated aliphatic, cycloaliphatic aromatic-aliphatic alcohol having from 3 to 25 carbon atoms or its carboxylic acid esters or ethers in the presence of an acid, or by reacting a trialkyl, trialkenyl- or triarylphosphine with an optionally substituted aliphatic, cycloaliphatic or aromatic-aliphatic halide having from 3 to 25 carbon atoms, wherein the reaction is conducted in a ternary solvent mixture, and wherein the quaternary phosphonium salt is of general formula I $$[R^1—P(R^2)_3]^+X^- \quad (I),$$

where
$R^1$ is an optionally substituted monounsaturated or polyunsaturated aliphatic, cycloaliphatic or aromatic-aliphatic group having from 3 to 25 carbon atoms,
$R^2$ is an alkyl, alkenyl or aryl group having from 1 to 9 carbon atoms,
X is an anion equivalent of an organic or inorganic acid and the trialkyl-, trialkenyl- or triarylphosphine is of general formula II $$P(R^2)_3 \quad (II),$$

where $R^2$ has the meaning given above, and the triakyl-, trialkenyl-, or triarylphosphine is reacted with a monounsaturated or polyunsaturated electophile of the general formula III or IV, $$R^1—Y \quad (III)$$

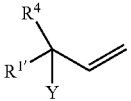
(IV)

where $R^1$ has the meaning given above, and
$R^{1'}$ is an optionally substituted, aliphatic, cycloaliphatic or aromatic-aliphatic hydrocarbon group having from 1 to 21 carbon atoms,
Y is OH, Cl, Br, O(CO)$R^3$ or OR$^3$ and $R^3$ is an aliphatic hydrocarbon group having from 1 to 6 carbon atoms, and $R^4$ is H or $CH_3$ and, when an electrophile of the general formula IV is reacted, $R^1$ in formula I is a structural element of the general formula V

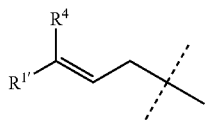

(V)

where $R^{1'}$ and $R^4$ have the meanings given above.

2. The process according to claim 1, wherein the quaternary phosphonium salt is of general formula I'

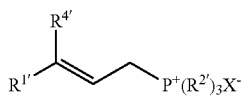

(I')

where $R^{1'}$ is an optionally substituted, aliphatic, cycloaliphatic or aromatic-aliphatic group having from 1 to 21 carbon atoms, $R^{2'}$ is an aryl group having from 1 to 9 carbon atoms, $R^{4'}$ is H or $CH_3$ and X is the anion equivalent of an organic or inorganic acid, and the trialkyl-trialkenyl- or triarylphosphine is of general formula II'

$P(R^{2'})_3$     (II'), where $R^{2'}$ has the meaning given above, and the the trialkyl-, trialkenyl- or triarylphosphine is reacted with a monounsaturated or polyunsaturated electrophile of the general formula IV or VI,

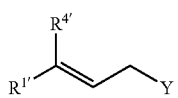

(VI)

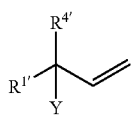

(IV)

where $R^{1'}$ and $R^{4'}$ have the meanings given above and

Y is OH, Cl, Br, $O(CO)R^3$ or $OR^3$ and $R^3$ is an aliphatic hydrocarbon group having from 1 to 6 carbon atoms.

3. The process according to claim 1, wherein the phosphine of the general formula II is triphenylphosphine.

4. The process according to claim 1, wherein the quaternary phosphonium salt is of the formula I"

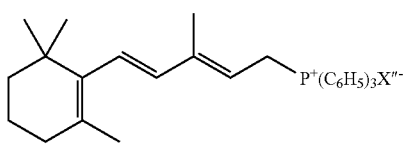

(I")

where

X" is Cl, Br or $HSO_4$, and the quaternary phosphonium salt is obtainable by reacting triphenylphosphine with β-vinylionol.

5. The process according to claim 1, wherein the ternary solvent mixture comprises of water, an alcohol having from 1 to 6 carbon atoms and a hydrocarbon having from 5 to 12 carbon atoms or a mixture of various hydrocarbons having from 5 to 12 carbon atoms.

6. The process according to claim 1, wherein the ternary solvent mixture consists of water, an alcohol having from 1 to 6 carbon atoms and a hydrocarbon having from 5 to 12 carbon atoms or a mixture of various hydrocarbons having from 5 to 12 carbon atoms.

7. The process according to claim 1, wherein the ternary solvent mixture consists of water, methanol and a hydrocarbon having 7 carbon atoms or a mixture of various hydrocarbons having 7 carbon atoms.

8. The process according to claim 1, wherein the ternary solvent mixture includes at least 5% by weight of water.

9. The process according to claim 1 wherein the ternary solvent mixture consists of 55-85% by weight of methanol, 10-25% by weight of heptane, and 5-20% by weight of water, and wherein the proportions of methanol, heptane, and water total 100% by weight.

10. The process according to claim 1, wherein the ternary solvent mixture is in the form of a two-phase system.

11. The process according to claim 1, wherein the acid is hydrochloric acid or sulfuric acid.

12. The process according to claim 1, further comprising separating the ternary solvent mixture, from the other components of the reaction mixture following completion of the reaction, and by optionally recirculating at least one of the components of the solvent mixture.

13. A method of synthesizing retinol (vitamin A), vitamin A acetate, vitamin A propionate, vitamin A palmitate, retinal retinoic acids, β-carotene, α-carotene, δ-carotene, zeaxanthin, astazanthin, canthaxanthin, lycopene, citranaxanthin, β-apo-8'-carotenal, crocetin, α-cryptoxanthin, β-cryptoxanthin, phytoene, lutein, bixin, capsanthin, capsorubin, β-apo-8'-carotenoic acid methyl ester, β-apo-8'-carotenic acid ethyl ester, β-apo-8'-caqrotenoic acid propionyl ester or β-apo-8'-carotenoic acid palmityl ester, comprising preparing the quaternary phosphonium salt of the general formula I by the process according to claim 1.

14. The process according to claim 2, wherein the phosphine of general formula II' is triphenylphosphine.

15. The process according to claim 1, wherein the ternary solvent mixture consists essentially of water, an alcohol having from 1 to 6 carbon atoms and a hydrocarbon having from 5 to 12 carbon atoms or a mixture of various hydrocarbons having from 5 to 12 carbon atoms.

16. The process according to claim 4, wherein the ternary solvent mixture consists essentially of water, an alcohol having from 1 to 6 carbon atoms and a hydrocarbon having from 5 to 12 carbon atoms or a mixture of various hydrocarbons having from 5 to 12 carbon atoms.

17. The process according to claim 4, wherein the ternary solvent mixture consists essentially of water, methanol and a hydrocarbon having 7 carbon atoms or a mixture of various hydrocarbons having 7 carbon atoms.

\* \* \* \* \*